(12) United States Patent
Ellscheid et al.

(10) Patent No.: US 7,149,570 B2
(45) Date of Patent: Dec. 12, 2006

(54) ALARM ACTIVATED ACOUSTIC MEASURING SIGNALS FOR PATIENT MONITORING

(75) Inventors: Klaus Ellscheid, Boeblingen (DE); Wilhelm Meier, Herrenberg (DE); Harald Greiner, Schwaikheim (DE); Jan Romeyn, De Hoef (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 259 days.

(21) Appl. No.: 10/493,685

(22) PCT Filed: Oct. 17, 2002

(86) PCT No.: PCT/IB02/04310

§ 371 (c)(1),
(2), (4) Date: Apr. 23, 2004

(87) PCT Pub. No.: WO03/037179

PCT Pub. Date: May 8, 2003

(65) Prior Publication Data
US 2004/0249296 A1  Dec. 9, 2004

(30) Foreign Application Priority Data
Oct. 27, 2001 (EP) ................... 01125737

(51) Int. Cl.
*A61B 5/04* (2006.01)
*A61B 5/00* (2006.01)

(52) U.S. Cl. ............ 600/519; 600/301; 600/310; 600/509

(58) Field of Classification Search ........ 600/301, 600/323–324, 514, 310, 481, 483, 509, 513, 600/519–520, 523; 340/539.12
See application file for complete search history.

(56) References Cited

U.S. PATENT DOCUMENTS

| | | | |
|---|---|---|---|
| 4,576,178 A * | 3/1986 | Johnson .............. | 600/483 |
| 4,653,498 A * | 3/1987 | New et al. ........... | 600/324 |
| 4,994,790 A | 2/1991 | Ishii et al. | |
| 5,226,416 A | 7/1993 | Bethune et al. | |
| 5,730,140 A * | 3/1998 | Fitch ................... | 600/514 |
| 6,449,501 B1 * | 9/2002 | Reuss .................. | 600/323 |
| 6,754,516 B1 * | 6/2004 | Mannheimer ........ | 600/323 |

FOREIGN PATENT DOCUMENTS

EP  0 909 551 A1  4/1999

* cited by examiner

*Primary Examiner*—Robert E. Pezzuto
*Assistant Examiner*—Jessica L. Reidel
(74) *Attorney, Agent, or Firm*—Fay, Sharpe, Fagan, Minnich & McKee LLP

(57) ABSTRACT

A system and a method for monitoring a physiological parameter of a patient providing a measurement-modulated acoustic signal (7) after/when a measurement value of the monitored physiological parameter exceeds an alarm limit.

12 Claims, 2 Drawing Sheets

| SpO2 | 100-%SpO2 -> x | x/24 -> y | 2^y -> z | 662Hz/z -> f | |
|---|---|---|---|---|---|
| 100% | 0 | 0 | 1 | | 662.0Hz |
| 76% | 24 | 1 | 2 | 662Hz/2 -> | 331.0Hz |
| 52% | 28 | 2 | 4 | 662Hz/4 -> | 165.5Hz |

ALARM ACTIVATED ACOUSTIC MEASURING SIGNALS FOR PATIENT MONITORING

BACKGROUND

The present invention relates to a patient system and method for monitoring a physiological parameter of a patient.

In today's patient monitoring systems, one of the most important tasks is to monitor condition and/or status of a patient, and to alarm medical staff in case that one or more monitored physiological parameters of the patient exceed pre-defined upper and/or lower alarm limits. These alarm limits may either be set manually, e.g. by medical staff, or can be set automatically, e.g. at start of a measurement or on user request. Each alarm limit may be set as fixed limit and/or can be based upon one or more current values of the physiological parameter of the patient e.g. determined by the patient monitoring system.

Various methods for determining alarm limits are disclosed e.g. in U.S. Pat. No. 4,994,790, U.S. Pat. No. 5,226,416, or EP-A-909551. Generally speaking, one or more limit values are determined based upon a starting value e.g. by adding or subtracting parameters specific offset values to or from these starting value, or by multiplying the starting value with a parameter specific factor.

When exceeding alarm limits, the patient monitoring system usually provides an acoustic signal for alerting the medical staff. However, it has been proved that erroneous alarming (i.e. unnecessary or faulty alarming) might lead to a situation wherein the medical staff simply switches off the acoustic alarming in order not to be bothered or confused by such kind of erroneous alarms. It is clear that such kind of situations have to be avoided since otherwise a patient's critical condition might not be noticed after alarms have been switched off.

A problem different from the erroneous alarming but which might lead to the same situation of switched off acoustic alarms, is the omnipresence of acoustic signals in particular from different patient monitoring systems. Particularly in intensive care environments with a plurality of different patient monitoring systems also for a plurality of different patients, it has been found that acoustic signals might be perceived as being disturbing for medical staff as well as for the patients. This in particular when there are several different acoustic signals at the same time. In such environments, it has been found that either the volume of acoustic signals will be reduced to a very low value, or the acoustic signals might even be switched off entirely, thus leading to the same situation as described above wherein a critical situation of a patient might not be noticed.

The problem has even become worse in recent years with the introduction of patient monitoring systems wherein a measuring signal indicative of a patient's physiological parameter is modulated on an acoustic signal. Examples for such measurement-modulated acoustic signals are: The modulation of a beep tone that is issued with every heart beat with the value of the oxygen saturation of a patient, and a whistling sound that is issued with every detected breath, modulated with the respiratory rate or something similar for an invasively measured blood pressure.

While on one hand such measurement-modulated acoustic signals provide useful information in a very intuitive way, clinical staff often feels disturbed by those acoustic signals, thus leading to the aforementioned situation of unnoticed critical situations as a result of switched off or volume-reduced acoustic signals.

It is therefore an object of the present invention to avoid situations wherein clinical staff feels disturbed by acoustic signals from patient monitoring systems.

SUMMARY

According to the invention, a patient monitoring system for monitoring a physiological parameter of a patient will provide a measurement-modulated acoustic signal after/when a measurement value of the monitored physiological parameter exceeds an alarm limit. The measurement-modulated acoustic signal represents an acoustic signal with the present measurement value acoustically modulated thereonto.

The term "exceeding" an alarm limit as used herein shall generally mean that the measurement value becomes either higher than an upper limit or lower than a lower limit, dependent on the respective situation.

In one embodiment, the measurement-modulated acoustic signal will be provided at a pre-defined acoustic volume independent of previous settings for the volume before the alarm limit has been exceeded. Thus, it can be made sure that the measurement-modulated acoustic signal will be heard even if all acoustic signals have been switched off before or reduced to a very low acoustic volume.

In one embodiment, the measurement-modulated acoustic signal will be switched off or significantly reduced in volume as soon as the measurement values return to "normal condition", i.e. the measurement values do not exceed one or more given alarm limits.

In another embodiment, the measurement-modulated acoustic signal will only be provided as long as alarm limits are exceeded, and will be switched off otherwise. This has the advantage that clinical staff becomes more sensible for such kind of acoustic signals, since they are only provided in critical situations.

According to another embodiment, the measurement modulated acoustic signal will be provided at a pre-defined high acoustic volume as long as and as soon as the measurement values are at an "alarm condition", i.e. the measurement values do exceed one ore more given alarm limits, and wherein the measurement modulated acoustic signal will be switched off or will be provided at a pre-defined low acoustic volume as long as and as soon as the measurement values are at an "normal condition", i.e. the measurement values do not exceed one or more given alarm limits.

Thus, acoustic signals are generally limited to (real) critical situations only. Furthermore the invention replaces pure alarming signals (with the only information content that there is an alarm) by information-related signals (indicating that there is an alarm and having an information content related to the source of the alarm) provided in alarming situations. The information-related alarming signals according to the invention directly refer to the source of the alarming situation by immediately providing acoustically coded information about the reason of the alarming situation. While pure alarming signals only indicate that there is an alarming situation without providing further information about the source or the nature of the alarm situation, the alarming allows to directly and intuitively perceiving the nature and source causing the alarming situation. Thus, immediate countermeasures in order to control the alarming situations can be initiated without loosing important time for figuring out what has been the reason for the alarming state.

Precious time can thus be saved that might be decisive in critical health situations. Since the measurement-modulated acoustic signal is switched off or at least significantly reduced in volume at normal conditions, the noise strain of patients and medical staff is reduced or avoided.

It is clear that the invention can be partly or entirely embodied or supported by one or more suitable software programs, which can be stored on or otherwise provided by any kind of data carrier, and which might be executed in or by any suitable data processing unit.

Other objects and many of the attendant advantages of the present invention will be readily appreciated and become better understood by reference to the following detailed description when considering in connection with the accompanied drawings. Features that are substantially or functionally equal or similar will be referred to with the same reference sign(s).

Advantages of the present application will be apparent to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figures 1, 2:
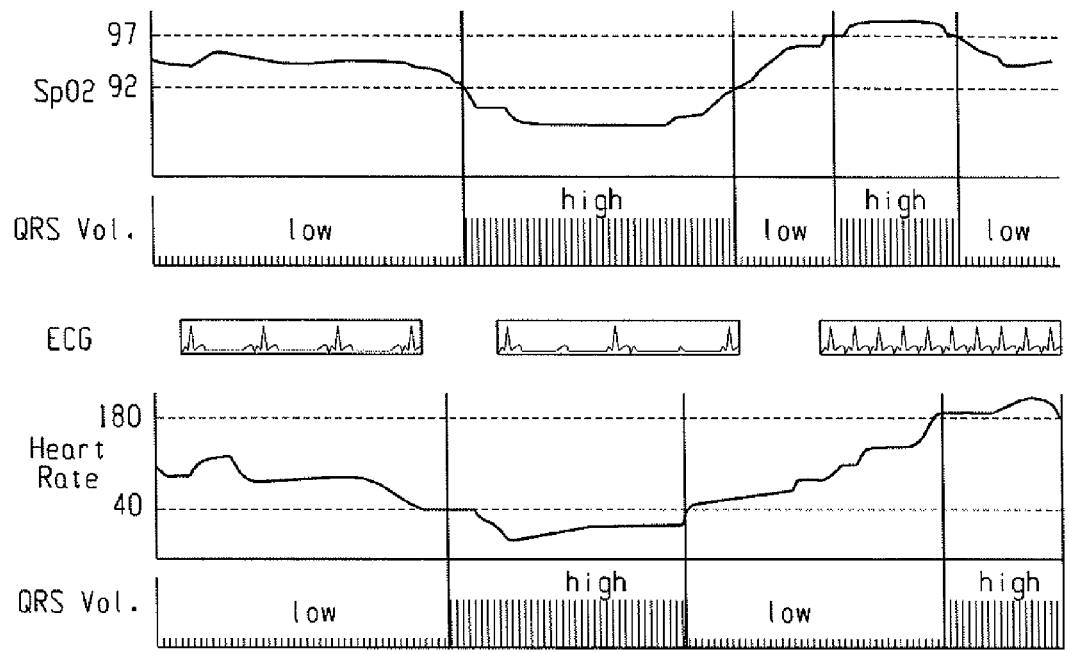
FIG. 1 shows a graph of an exemplary time course of a patients ECG with SpO2 and Heart Rate.
FIG. 2 shows a table wherein the frequency of a beep tone is assigned to the SpO2 value.

FIG. 1 shows how the volume of the QRS beep is linked to either the violation of an SpO2 or Heart Rate Alarm Limit. the QRS beep is a tone that is issued every time a heartbeat is detected in the ECG signal of a patient. The Heart Rate is measured in beats per minute. A usual monitoring system permanently provides an acoustic signal, namely a beep tone, with every heart beat or QRS. This acoustic signal is preferably modulated with the SpO2 value. Therefore a patient monitor can be configured so that the frequency of the beep tone depends on the currently measured SpO2 value, e.g. defined as follows:

$$F=662\ HZ/(2^{[1/24](100-\%SPO2)]}.$$

FIG. 2 shows examples of audible frequencies for SpO2 values of 100, 76 and 52%.

A usual monitoring system provides this insofar measurement-modulated acoustic signal always at the same acoustic volume. Normal alarming behavior of such a usual patient monitor is that if a parameter, e.g. SpO2 or Heart Rate, violates an upper limit (e.g. SpO2: 97, Heart Rate: 180) or lower limit (e.g. SpO2: 92, Heart Rate: 40) a special alarm tone is issued. This special alarm tone is significantly different from the usual normal beep tone of the measurement-modulated acoustic signal. If the alarm system is configured to latching alarms the alarm tone even sounds beyond the limit violation until it has been manually acknowledged by pressing a silence button. Also, in case of an alarm it is very helpful to hear the QRS beep modulated with SpO2 value.

There is significantly less sound or no sound at all being heard in clinical environment if e.g. an SpO2 or a heart rate are within their set limits. But if an alarm occurs the volume of the QRS sound is turned on (or increased) as long as the alarm exists or in case of latching alarms until it is acknowledged manually. This means that in case of an alarm the clinical operator gets all the information needed by his attention being pulled to a sound that is familiar to him and that conveys all the information needed. The information conveyed in this case is: the variation in the SpO2 value and the heart rate. Just listening to the changes of the QRS beep the clinical operator would know immediately what is going on. An additional special alarm sound that is the same for all parameters and thus needs visual verification on a patient monitor display would not be necessary.

A Heart Rate alarm can be announced the same way by issuing a QRS beep that has no frequency modulated sound. The same logic then applies to arrhythmia alarms that do not particularly announce the violation of an alarm limit but irregularities in the Heart Rate. As long as a Heart Rate is regular it is just an unnecessary background noise that only then becomes vital and needs to be heard if it becomes irregular.

To alarm on both parameters, it is still clear from the signal which parameter of the two is in alarm. If both parameters are in alarm at the same time only the combined tones as for SpO2 would be used.

This can be extended to other parameters than SpO2 and Heart Rate e.g. for Respiratory signals. In this a typical respiratory sound triggered by each breath would be turned on only in case of an alarm.

Figure 3:
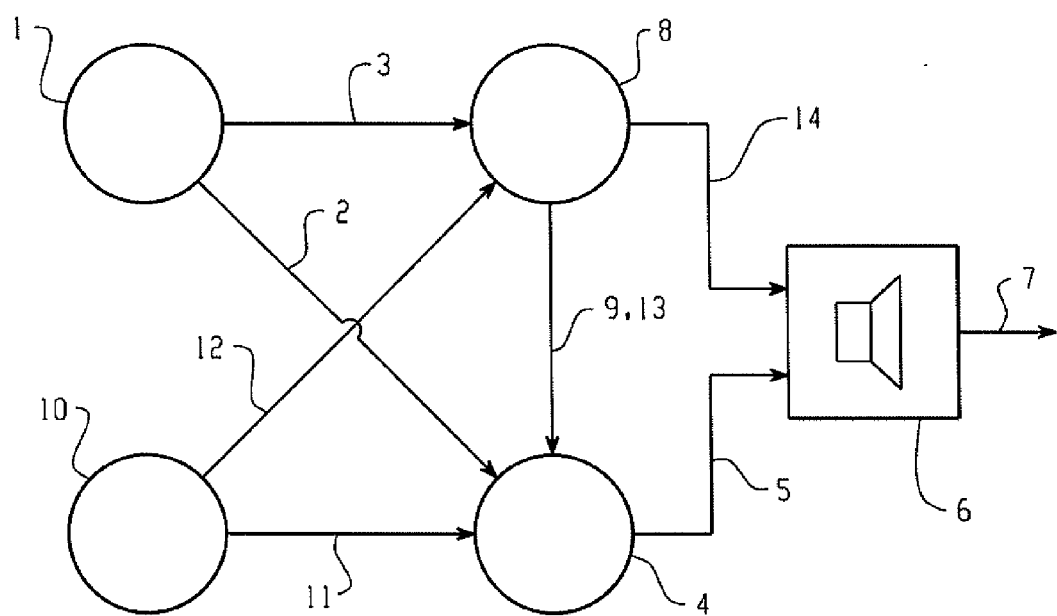
FIG. 3 shows a schematic view of a system according to the invention.

The technical implementation comprises according to FIG. 3 an ECG unit 1 providing a QRS trigger signal 2 at normal condition and additionally a heart rate alarm signal 3 at alarm condition. The ECG unit 1 sends the QRS trigger signal 2 to a QRS beep generator 4 provided for generating beep tone signals 5 with different frequencies depending from a current SpO2 value. The QRS beep generator 4 is connected to a loudspeaker unit 6 provided for generating acoustic signals 7 according to the incoming beep one signals 5 of the QRS beep generator 4.

The ECG unit 1 sends the heart rate alarm signal 3 to an alarm unit 8, if the monitored heart rate exceeds an alarm limit, e.g. if the heart rate violates an upper or lower limit or if the heart rate becomes irregular. In case of a heart rate alarm the alarm unit 8 generates an alarm trigger in form of a heart rate alarm signal 9 and sends it to the QRS beep generator 4.

The monitoring system comprises also a SpO2 unit 10 providing a SpO2 value signal 11 at normal condition and additionally a SpO2 alarm signal 12 at alarm condition. The SpO2 unit 10 sends the SpO2 value signal 11 to the QRS beep generator 4 modulating the QRS signal 2 of the ECG unit 1 with the SpO2 value alarm signal 11.

The SpO2 unit 2 sends the SpO2 alarm signal 12 to the alarm unit 8, if the monitored SpO2 value exceeds an alarm limit, e.g. if the SpO2 value violates an upper or lower limit or if the SpO2 value becomes irregular. In case of a SpO2 value alarm the alarm unit 8 generates an alarm trigger in form of a SpO2 value alarm signal 13 and sends it to the QRS beep generator 4.

The monitoring system or method according to the invention works as follows:

At normal conditions, e.g. the heart rate and the SpO2 values do not exceed its alarm limits, the ECG unit 1 only sends the QRS trigger signal 2 to the QRS beep generator 4. Also the SpO2 unit 10 only sends the SpO2 value signal 11 to the QRS beep generator 4. As long as the monitored parameters (SpO2 and heart rate) are regular the QRS beep generator 4 generates the QRS beep tone signal 5, i.e. a SpO2 modulated heart rate signal, with a very low acoustic volume and sends it to the loudspeaker 6 generating the corresponding acoustic signal 7. In another embodiment the QRS beep generator does not generate any QRS beep tone signals 5 at all as soon as the conditions are normal, therefore the loudspeaker 6 is quiet. Therefore at normal conditions there is no disturbing noise in the clinical environment of the monitoring system.

In alarm condition, e.g. if the SpO2 value violates an alarm limit, the SpO2 unit 10 sends the SpO2 alarm signal 12 to the alarm unit 8 which generates the SpO2 value alarm signal 13. As soon as the QRS beep generator 4 receives this SpO2 value alarm signal 13, the QRS beep generator 4 generates a corresponding QRS beep tone signal 5 and sends it to the loudspeaker 6 generating the corresponding acoustic signal 7. This acoustic signal 7 preferably will be provided at a pre-defined acoustic volume which is independent of previous settings for the volume before the alarm limit has been exceeded. If the QRS beep generator 4 provides at normal condition a QRS beep tone signal 5 with a small acoustic volume, the QRS beep tone signal 5 at alarm condition has a significantly louder acoustic volume. Therefore at alarm condition the medical staff gets information-related acoustic alarming signals which directly refer to the source of the alarming situation by immediately providing acoustically coded information about the reason of the alarming situation.

The monitoring system and the monitoring method can be partly or entirely embodied or supported by at least one software program, which is executed in or by a conventional monitoring system.

In contrast, a conventional monitoring system needs a direct connection 14 between the alarm unit 8 and the loudspeaker 6. Therefore the alarm unit 8 of a conventional system generates an alarm tone signal and sends it to the loudspeaker 6 if one of the monitored parameters violates one of the alarm limits. At a conventional system this alarm signal can replace or overlay the normal signal which is at normal condition permanently generated by QRS beep generator 4 and loudspeaker 6. Although the direct connection 14 is depicted in the embodiment of FIG. 3, the present monitoring system does not need this direct connection 14. The direct connection 14 is only depicted to illustrate, that the present system can be partly or entirely embodied in a conventional monitoring system.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having described the preferred embodiments, the invention is now claimed to be:

1. A patient monitoring system for monitoring at least two physiological parameters of a patient, the system comprising:
    an electrocardiograph ECG which monitors the patient's cardiac heart rate;
    a second physiological parameter monitor which monitors values of a second physiological parameter of the patient;
    an acoustic signal generator which generates acoustic signals;
    a beep generator connected with the ECG monitor and the second physiological parameter monitor which generates a beep tone at a characteristic point in each cycle of said cyclic heart rate at a tone which varies in accordance with the monitored values of the second physiological parameter, the beep generator being connected with the acoustic signal generator to generate a series of beeps whose rate is indicative of the cyclic heart rate and whose tone is indicative of the monitored values of the second physiological parameter; and,
    an alarm unit which causes a volume of the acoustic signal to change from switched off or a lower volume to a predefined higher acoustic volume in response to the monitored values of one or both of the second monitored physiological parameters or the monitored heart rate exceeding an alarm limit.

2. The system of claim 1, wherein the pre-defined acoustic volume is independent of previous settings for the volume before the alarm limit has been exceeded.

3. The system according to claim 1, wherein the acoustic signal is only generated as long as one or more alarm limits are exceeded, and is switched off otherwise.

4. The system according to claim 1, wherein the acoustic signal is generated at the pre-defined higher acoustic volume as long as and as soon as the second monitored values or the heart rate are at an alarm condition and the acoustic signal is switched off or is generated at the lower acoustic volume as long as and as soon as the second measurement values and the heart rate do not exceed one or more given alarm limits.

5. A method for monitoring at least two physiological parameters of a patient and providing a measurement-modulated acoustic signal after/when a measurement value of the monitored physiological parameters exceeds an alarm limit, the method comprising:
    measuring a value of a first cyclic monitored physiological parameter;
    measuring a value of a second monitored physiological parameter;
    in response to a measured value of any physiological parameter exceeding an alarm limit, providing the measurement-modulated acoustic signal at a predefined high acoustic volume, the acoustic signal including a series of beeps whose rate varies in accordance with the measurement values of the first cyclic monitored physiological parameter and whose tone varies in accordance with the measurement values of the second monitored physiological parameter; and,
    in response to no alarm limits being exceeded, reducing the acoustic volume of the measurement modulated acoustic signal to a low volume or switching the measurement-modulated acoustic signal off.

6. The method according to claim 5, wherein the measurement-modulated acoustic signal is only provided as long as alarm limits are exceeded, and is switched off otherwise.

7. A software program or product stored on a data carrier, for executing the method of claim 5 when run on a data processing system.

8. The method according to claim 5 wherein the first application monitored physiological parameter is heart rate and one beep of the measurement modulated acoustic signal is provided at a common characteristic point in each cardiac cycle of the patient.

9. The method according to claim 8 wherein the second monitored physiological condition is SpO2, such that the beeps of the measurement modulated acoustic signal are provided at a periodicity indicative of heart rate with a tone or frequency indicative of a measured blood oxygen level.

10. A patient monitoring system comprising:
a signal modulator which receives a first measured physiological parameter value from at least a first physiological parameter monitor and provides an output signal whose pulse rate or tone is modulated with the first measured parameter value;
an acoustic signal generated which converts the output signal from the signal modulator into a measurement modulated acoustic signal; and,
an alarm unit which causes the measurement-modulated acoustic signal to be provided constantly at a preselected high volume whenever and for as long as a measured physiological value exceeds its alarm limit and causes the measurement-modulated acoustic signal to be one of off or provided at a low volume whenever no measured physiologic value exceeds its alarm limit.

11. The patient monitoring system according to claim 10 wherein the alarm unit causes the measurement-modulated acoustic signal to be off whenever no measured physiological parameter exceeds its alarm limit such that the measurement-modulated acoustic signal is provided only when a measured physiological parameter value exceeds its alarm limit.

12. The patient monitoring system according to claim 11 wherein the signal modulator further receive a second measured physiological parameter value from a second physiological parameter monitor and modulates the pulse rate of the measurement-modulated acoustic signal with one of the first and second measured physiological parameter values and modulates the tone of the measurement modulated acoustic signal with the other of the first and second measured physiological parameter values.

* * * * *